US00PP12727P2

(12) United States Plant Patent
Utecht

(10) Patent No.: US PP12,727 P2
(45) Date of Patent: Jun. 25, 2002

(54) NEW GERANIUM PLANT NAMED 'FISHELEN'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/323,470

(22) Filed: Jun. 1, 1999

(51) Int. Cl.[7] ..... A01H 5/00
(52) U.S. Cl. ..... Plt./327
(58) Field of Search ..... Plt./327, 328, 329

(56) References Cited

FOREIGN PATENT DOCUMENTS

| | | |
|---|---|---|
| PL | 469 | 12/1998 |
| CA | 98-1362 | 4/1998 |
| CH | 98-26-1427 | 4/1998 |
| DE | PEL 1360 | 9/1996 |
| EP | 97/0958 | 9/1997 |

OTHER PUBLICATIONS

Licensing agreement for 'Fisrosimo', http://www.sicasov-.com/baremes/f–fl9899.htm, 1999/2000.*
Kesler, Greenhouse Production of Zonal Geranium, http://www.aces.edu/department/extcomm/publications/anr/anr–1106/anr–1106.htm, Apr. 1998.*
Pelargonium 1998, Pelfi Fischer, Hillscheid Germany, p. 6 (1998/1999).

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of geranium plant named 'Fishelen', as described and illustrated, and particularly characterized by the combined features of bright salmon-pink cup-shaped flowers with a small white eye; medium green foliage with strong zonation; medium sized, well-branched, round plant habit; and early to medium flowering respone.

1 Drawing Sheet

BACKGROUND OF THE INVENTION

The present invention comprises a new and distinct cultivar of geranium plant, botanically known as *Pelargonium zonale*, and hereinafter referred to by the cultivar name 'Fishelen'.

'Fishelen' is a product of a planned breeding program which had the objective of creating new geranium cultivars with bright salmon-pink cup-shaped flowers, medium green foliage, and early to medium flowering response.

'Fishelen' was originated from a hybridization made by the inventor, Angelika Utecht, in a controlled breeding program in Galdar, Gran Canaria, Spain, in 1993. The female parent was a hybrid seedling, designated no. 978/6, characterized by light salmon-pink, semi-double flowers, dark green foliage with weak zonation, and compact plant habit, which had been derived from crosses between salmon-pink colored commercial varieties 'Schöne Helena' (U.S. Plant Pat. No. 5,374), 'Fidelio' (U.S. Plant Pat. No. 5,752), and 'Regina' (unpatented) with a tetraploid line of 'Stadt Bern' (unpatented).

The male parent of 'Fishelen' was the commercial variety 'Fishog' (U.S. Plant Pat. No. 8,174), having light salmon-pink and white flowers, large, distinctly zoned, medium green leaves, and moderately vigorous growth.

'Fishelen' was selected as one flowering plant within the progeny of the stated cross by the inventor, Angelika Utecht, in 1994 in a controlled environment in Galdar, Gran Canaria, Spain.

The first act of asexual reproduction of 'Fishelen' was accomplished when vegetative cuttings were taken from the initial selection in autumn 1994 in a controlled environment in Galdar, Gran Canaria, Spain by Angelika Utecht. Horticultural examination of plants grown from the cuttings of the clone, initiated in May 1995 in Hillscheid, Federal Republic of Germany, and continuing thereafter, has demonstrated that the combination of characteristics as herein disclosed for 'Fishelen' are firmly fixed and are retained through successive generations of asexual reproduction.

BRIEF DESCRIPTION OF THE INVENTION

The following traits have been repeatedly observed and are determined to be basic characteristics of 'Fishelen', which in combination distinguish this geranium as a new and distinct cultivar:

1. weakly semi-double, salmon colored flowers with a small white eye;
2. semi-spherically shaped, medium to large umbels;
3. medium green foliage with strong zonation;
4. medium sized, round, and well-branched plant habit;
5. early to medium flowering response, and permanent flowering; and
6. good outdoor performance even in rainy periods.

'Fishelen' has not been observed under all possible environmental conditions. The phenotype of the new cultivar may vary significantly with variations in environment such as temperature, light intensity and daylength without any change in the genotype of the plant. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fishelen' is the variety 'Schöne Helena'. In comparision to 'Schöne Helena', 'Fishelen' has a more intense salmon flower color, with less distinct white margin and with a small white 'eye' at the base of the upper petals, and somewhat larger and more cup-shaped florets, while 'Schoöne Helena' develops more inner petals. Furthermore, 'Fishelen' has much stronger zonation on leaves, and somewhat better branching characteristics thereby developing a more rounded and more uniform plant habit.

BRIEF DESCRIPTION OF THE DRAWING

The accompanying color photographic drawing shows typical flower and foliage characteristics of 'Fishelen' with colors being as true as possible with illustrations of this type.

DETAILED BOTANICAL DESCRIPTION

The measurements were taken in Langley, British Columbia, Canada, on May 26, 1998, 10 weeks after planting of rooted cuttings into 15-cm pots. The plants had not been pinched. In the following description, color references are made to The Royal Horticultural Society Colour Chart (R.H.S.). The color values were determined indoors from flowers developed in a greenhouse in May 1998 in Hillscheld, Germany.

Classification:

*Botanical.*—A hybrid of the species *Pelargonium zonale L'Hérit.*

*Commercial.*—Zonal geranium, cv. 'Fishelen'.

Inflorescence:

*Umbel.*— Shape: Semi-spherical. Average diameter: 116 mm. Average depth: 48 mm. Peduncle length: 138 mm. Peduncle color: Medium green, RHS 143 A. Peduncle texture: Slightly rough, with weak pubescence. Pedicel length: 24 mm. Pedicel color: Light green in the middle part, RHS 144 B, no anthocyanin under greenhouse conditions. Number of flowers per umbel: Approximately 30. Lastingness of the individual umbel: Average for the commercial zonal varieties with relatively large flower heads, lasting approximately 16–17 days in greenhouse conditions in spring at a minimum temperature of 18° C.

*Corolla.*—Average diameter: 47 mm. Form: Weakly semi-double. Shape: Cup-shaped, open in the middle and nearly round. Number of petals: 5–7. Number of petaloids: 1–2. Color of petaloids: RHS 41 B–41 C, with whitish filament or base. Color (general tonality from a distance of three meters): Salmon-pink, little white. Color of upper petals: Main color: RHS 41 B–C. Margin: RHS 43 D. Markings of upper petals: No distinct markings, small white 'eye' at the base. Color of lower petals: Approximately RHS 43 D. Markings of lower petals: Main color is RHS 41 B–C, near the margin is RHS 43 D. Color of lower surface of petals: RHS 43 D or lighter. Color of sepals: Light green, RHS 144 B. Number of sepals: 5. Texture of sepals: Smooth, apart from the weak pubescence.

*Bud (immediately before unfolding of the petals).*—Shape: Elliptical. Color (sepals): Light green, RHS 143 B–C. Color (petals): Salmon, RHS 40 B or lighter. Length: Approximately 19 mm. Width: Approximately 9 mm.

*Reproductive organs.*—Androecium: Approximately 5 fertile anthers, whitish filaments, yellow-orange pollen. Gynoecium: 5–6-lobed stigma, reddish style and stigma, approximately RHS 43 A. Fertility/seed set: A few seeds are developed, mainly in late summer and autumn.

*Spring flowering response period.*—In Hillscheild, Germany, in 1998, plants had on average 0.7 flowers opened 11 weeks after planting of unrooted cuttings.

*Outdoor flower production.*—Medium to many inflorescence, continuous development of flowers throughout the summer.

*Blooming habit.*—Continuous flowering from about May to mid-September; after which flowering may be poor depending on general conditions and light intensity. There is no noticeable fragrance apart from the slightly aromatic scent that is typical of all zonal varieties.

*Lastingness of the individual bloom.*—Typical/average for semi-double flowers of zonal varieties, lasting approximately 9 days in greenhouse conditions in spring at a temperature of 18° C.; due to the open cup-shape, they are not susceptible to unfavorable weather conditions.

*Durability.*—Average shatter resistance for a semi-double flowered variety, good rain resistance and little fading or burning of flowers, relatively good outdoor performance.

Plant:

*Foliage.*—Form: Kidney-shaped with an open base. Margin: Bicrenated. Texture: Surface slightly velvety, dull. Size of leaf: 89 mm. Color of upper surface: Medium green, RHS 137 C. Color of lower surface: RHS 137 D. Color of zonation: Strong, brown, approximately RHS 166 A, distinctness is 7 (in the range from 1="no zonation" to 9="very strong"). Tolerance of botrytis: Average.

*General appearance and form.*—Internode length: 10–20 mm. Branching pattern: 4.7 naturally-occurring branches. Size of foliage: 13.0 c m high and 31.8 cm in diameter.

I claim:

1. A new and distinct cultivar of geranium plant named 'Fishelen', as described and illustrated.

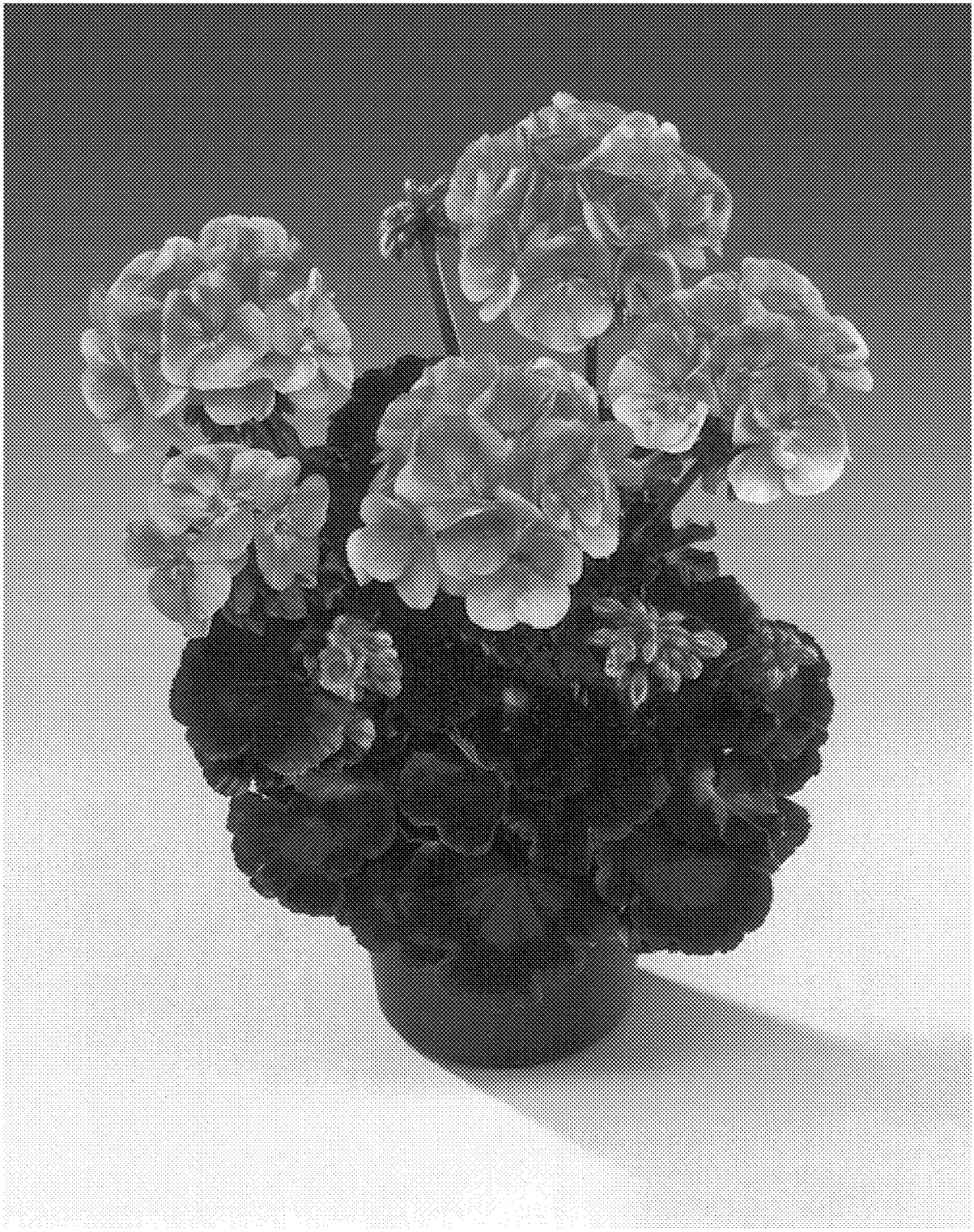

* * * * *